United States Patent [19]
Quinn

[11] Patent Number: 6,077,243
[45] Date of Patent: Jun. 20, 2000

[54] RETENTION BALLOON FOR A CORPOREAL ACCESS TUBE ASSEMBLY

[75] Inventor: David G. Quinn, Grayslake, Ill.

[73] Assignee: C.R. Bard, Inc., Murray Hill, N.J.

[21] Appl. No.: 09/174,722

[22] Filed: Oct. 19, 1998

Related U.S. Application Data

[60] Continuation-in-part of application No. 08/847,116, May 1, 1997, Pat. No. 5,910,128, which is a division of application No. 08/734,630, Oct. 18, 1996, Pat. No. 5,860,952, which is a continuation-in-part of application No. 08/583,930, Jan. 11, 1996, abandoned.

[51] Int. Cl.$^7$ ...................................................... A61M 25/00
[52] U.S. Cl. ...................... 604/93; 604/174; 128/DIG. 26
[58] Field of Search .............................. 604/174, 93, 153, 604/176, 264, 180, 523; 128/DIG. 26

[56] References Cited

U.S. PATENT DOCUMENTS

| | | |
|---|---|---|
| 3,915,171 | 10/1975 | Shermeta . |
| 4,261,363 | 4/1981 | Russo . |
| 4,356,824 | 11/1982 | Vazquez . |
| 4,419,094 | 12/1983 | Patel . |
| 4,435,174 | 3/1984 | Redmound et al. . |
| 4,533,349 | 8/1985 | Bark . |
| 4,543,089 | 9/1985 | Moss . |
| 4,576,603 | 3/1986 | Moss . |
| 4,594,074 | 6/1986 | Andersen et al. . |
| 4,642,092 | 2/1987 | Moss . |
| 4,645,492 | 2/1987 | Weeks . |
| 4,666,433 | 5/1987 | Parks . |
| 4,685,901 | 8/1987 | Parks . |
| 4,699,616 | 10/1987 | Nowak et al. . |
| 4,701,163 | 10/1987 | Parks . |
| 4,717,385 | 1/1988 | Cameron et al. . |
| 4,795,430 | 1/1989 | Quinn et al. . |
| 4,798,592 | 1/1989 | Parks . |
| 4,834,712 | 5/1989 | Quinn et al. . |
| 4,900,306 | 2/1990 | Quinn et al. . |
| 4,932,943 | 6/1990 | Nowak . |
| 4,981,471 | 1/1991 | Quinn et al. . |
| 4,986,815 | 1/1991 | Schneider . |
| 5,073,166 | 12/1991 | Parks et al. . |
| 5,073,170 | 12/1991 | Schneider . |
| 5,125,897 | 6/1992 | Quinn et al. . |
| 5,267,967 | 12/1993 | Schneider . |
| 5,267,969 | 12/1993 | Hirsch . |
| 5,308,325 | 5/1994 | Quinn et al. . |
| 5,342,321 | 8/1994 | Potter . |
| 5,370,625 | 12/1994 | Schichman . |
| 5,439,444 | 8/1995 | Andersen et al. . |
| 5,451,212 | 9/1995 | Anderson . |
| 5,484,420 | 1/1996 | Russo . |
| 5,569,200 | 10/1996 | Umeno et al. . |

FOREIGN PATENT DOCUMENTS 0 574 961 A1  12/1993  European Pat. Off. .

*Primary Examiner*—John D. Yasko
*Attorney, Agent, or Firm*—Richard G. Lione; Brinks Hofer Gilson & Lione

[57] ABSTRACT

An improvement in an internal bolster for a corporeal access tube assembly wherein a retention balloon is preformed of relatively thick silicone rubber film. The balloon includes parallel front and rear sidewalls connected by a semi-circular treadwall, the front sidewall having a front retention surface thereon with a radial width equal to the radius of the treadwall. Annular sleeves at the inner periphery of each sidewall are sealed to the outer surface of a tube segment. Each sleeve extends forwardly of its corresponding sidewall.

15 Claims, 3 Drawing Sheets

RETENTION BALLOON FOR A CORPOREAL ACCESS TUBE ASSEMBLY

RELATED APPLICATION

This application is a continuation-in-part of application Ser. No. 08/847,116, filed May 1, 1997, now U.S. Pat. No. 5,910,128 and entitled Retention Balloon And Corporeal Access Tube Assembly, which is a division of application Ser. No. 08/734,630, filed Oct. 18, 1996, now U.S. Pat. No. 5,860,952 entitled Corporeal Access Tube Assembly and Method which, in turn, is a continuation-in-part of application Ser. No. 08/583,930, filed Jan. 11, 1996, now abandoned entitled Replacement Gastrotomy Tube.

FIELD OF THE INVENTION

This invention relates generally to medical catheters. It relates particularly to catheters used to access the stomach and/or intestine, or the bladder, through a stoma or ostomy in the abdominal wall.

BACKGROUND OF THE INVENTIONS

The need to artificially introduce food into the gastrointestinal tracts of individuals who can not eat, or will not eat, has been well-known throughout and even prior to this century. Before the mid-1970's, feeding was done nasogastrically with red rubber or polyvinylchloride feeding tubes. The use of enteral feeding by means of nasogastric tubes expanded dramatically in the late 1970's with the introduction of tubes constructed of either silicone rubber or polyurethane. Being constructed of stronger materials, these tubes incorporated thinner walls, and were therefore smaller in outside diameter. These smaller tubes were easier to insert and more comfortable for the patient, and their introduction resulted in a very rapid growth of enteral nutrition via the nasogastric route, and increased interest in enteral nutrition in general.

By the 1980's problems with nasogastric feeding were recognized by clinicians and the advantages of direct gastrostomy access into the stomach through the abdominal wall had been described by Vazquez in U.S. Pat. No. 4,356,824, and by Moss in U.S. Pat. No. 4,543,085. Refinements in securing gastrostomy tubes in the patient were described by Parks in U.S. Pat. No. 4,666,433 and in U.S. Pat. No. 4,685,901.

The 1980's also saw the refinement of methods for forming the gastrostomy stoma. Prior to the 1980's, the stoma or gastrostomy was formed surgically by the Stamm procedure, which required a surgical laporatoratomy to insert the tube, usually a latex urologic Foley retention catheter. A new method, called a "PEG", or Percutaneous Endoscopic Gastrostomy, eliminated the need for a surgical gastrostomy to place the gastrostomy tube and dramatically expanded the interest in the use of direct gastrostomy tubes. The advantages of PEGs and the PEG technique were described by Quinn et al. in U.S. Pat. No. 4,795,430. The word "PEG" is used herein to identify both the tube and the procedure.

Gastrostomy tubes can generally be organized into three main groups, the third of which includes two subgroups:

1. SPECIALTY TUBES placed at the time of gastric surgery by the Stamm technique. The Moss and Vazquez patent tubes are examples of this type.

2. PEG TUBES which are used to form the initial stoma or gastrostomy.

3. REPLACEMENT TUBES which are used to replace PEG TUBES after a period of time because a PEG TUBE has worn out with use, or because a device which is more specific to the patient's need is required. These tubes are inserted into the original stoma created by either the PEG TUBE or the Stamm technique.

a. LOW PROFILE REPLACEMENT TUBES which are preferred for active patients who wish to conceal the tube's outer fitments during periods when they are not receiving feeding formula. The background for this type of replacement tube is described by Quinn et al. in U.S. Pat. No. 5,125,897.

b. SIMPLE REPLACEMENT tubes which are less complicated and less expensive are used for patients who are not active and have no need to hide their device. These devices are direct modifications of the original urologic Foley catheters used in early gastrostomies. They are described by Parks in U.S. Pat. No. 4,666,433.

With some exceptions within individual designs, gastrostomy tubes or tube assemblies of the aforedescribed types each incorporate the following seven features or components:

1. A tube to carry the enteral feeding formula into the stomach and or the intestine.

2. An outflow port in the distal end of the tube. The port or ports may be incorporated in the end or the sidewall of the tube. They may also be incorporated in a separate, molded bolus fastened to the distal end of the tube.

3. An administration set connector attached to the proximal end of the tube, which is outside of the patient.

4. A distal end retention device or internal bolster to hold the tube in the stomach, e.g., an inflatable balloon or a molded retention shape which can be deformed with a stylet for insertion and removal.

5. An external bolster to secure the tube at the point where it exits the skin. This bolster maintains the proper distance between the external bolster and the internal retention device, a distance corresponding to the combined thickness of the individual patient's skin, abdominal wall and stomach wall at the site of the gastrostomy.

6. An anti-reflux valve to prevent leakage of gastric acids from the patient when the administration set is being changed or when violent coughing causes excessive back pressure.

7. A measurement system to measure the patient's abdominal wall thickness so that the tube length between the retention device and the external bolster can be adjusted to match this thickness.

In addition to gastrostomy, tubes or tube assemblies of this type are used to administer drugs to, or drain urine from, the bladder. Such tubes or tube assemblies are referred to as suprapubic catheters and comprise the same seven features or components referred to above in the context of gastronomy tubes or tube assemblies. However, they access the bladder through a stoma formed in the abdominal wall above the bladder or pubic area.

The feature of gastrostomy and other corporeal access tube assemblies with which the present invention is concerned is the distal end retention device. Distal end retention devices take many forms. Some are simply an inflatable balloon which is collapsible to permit removal. Others use non-inflatable, preformed structures which can be physically deformed to permit removal. Others are combinations of these approaches. Shermeta U.S. Pat. No. 3,915,171, Quinn et al. U.S. Pat. No. 4,981,471 and Andersen et al. U.S. Pat. No. 5,439,444 disclose exemplary devices.

Tubes with inflatable silicone retention balloons are easy to insert because the uninflated balloons are formed completely flat against the tube wall. However, they are unreliable because the silicone balloon walls, which are stretched thin when expanded, tend to break easily. Preformed, molded internal retention devices must be deformed with a stylet and are difficult to insert and remove, although they are generally reliable once they are in place.

SUMMARY OF THE INVENTION

It is an object of the present invention to provide an improved retention balloon or internal balloon bolster for a corporeal access tube assembly.

It is another object to provide an internal balloon bolster which improves the pull-out resistance characteristics of the access tube assembly from a stoma while in its retention configuration.

It is another object to provide an internal balloon bolster which permits pulling the access tube assembly from a stoma with minimal pull-out force while in its pull-out configuration.

It is still another object to provide an internal balloon bolster which is particularly well suited for pediatric use.

The foregoing and other objects of the present invention are realized in a corporeal access tube assembly including a tube segment and a balloon bolster. The tube segment is molded of silicone rubber and includes a coil spring support in one portion and another portion which does not contain a coil spring. The balloon bolster encircles the other portion of the tube segment.

The balloon bolster includes a balloon preformed of silicone rubber film in a tire-shaped, retention configuration. It is supported by a gas (preferably air) under ambient pressure in this configuration. A deflation lumen extends through the tube segment into communication with the balloon, but is normally plugged to prevent gas from escaping.

The balloon includes front and rear sidewalls which extend parallel to each other, and a semi-circular treadwall connecting them. The front sidewall has a flat front retention surface on it with a width equal to the radius of the semi-circular outer surface on the treadwall.

The sidewalls and treadwall are all the same thickness, which is preferably between about 0.020 and 0.030 inches. Silicone rubber film in this thickness range is relatively resistant to stretching in the context of this invention so that the size of the balloon remains constant.

The annual inner periphery of each sidewall has a bead formed thereon, and each of these beads is fastened to the outer surface of the tube segment. According to the invention, each sidewall bead comprises a cylindrical sleeve which extends away from the outlet port of the tube segment and is glued in sealing relationship to the outer surface of the tube segment.

In one embodiment of the invention, the sidewalls and treadwall are 0.030 inches thick and the cylindrical sleeve which forms the bead on the front sidewall is also 0.030 inches thick. This sleeve extends forwardly of the front sidewall, i.e., toward the external bolster, for a predetermined distance. The cylindrical sleeve which forms the bead on the rear sidewall is only 0.015 inches thick. This sleeve extends forwardly of the rear sidewall so that it is inside the balloon when the balloon is mounted on the tube segment. The length of this sleeve is preferably slightly less than the length of the front sidewall sleeve.

In another embodiment of the invention, the sidewalls and treadwall are 0.020 inches thick. Both the front and rear sidewall sleeves are 0.015 inches thick. Again, the length of the rear sidewall sleeve is preferably slightly less than the length of the front sidewall sleeve.

In either embodiment, when the balloon is in its preformed retention configuration, and air is trapped therein, force applied to the flat retention surface of the balloon tends to deform the balloon rearwardly. This increases the pressure inside the balloon. Because the width of the retention surface and the radius of the treadwall surface are equal, and the walls do not readily stretch, the balloon substantially resists further deformation. At the same time, the increased pressure within the balloon is effective on the rear sidewall sleeve and causes the sleeve to seat even more tightly against the tube surface.

Because the rear sidewall sleeve extends away from the outlet port for the tube segment, the rear sidewall is flush with the outlet port, i.e., the tube segment does not protrude. As a result, a flat surface is presented to gastric mucosa opposite it in the stomach, for example.

When it is desirable to remove the tube assembly from a stoma, the lumen is opened to provide a path for trapped air to leave the balloon. The balloon can then easily fold rearwardly of the outlet port in the tube segment as it is pulled through the stoma. Because the rear sleeve extends forwardly, only the front sidewall of the rearwardly folded balloon overlies it. Double (rather than triple) silicone film thickness results at the rear sleeve and, because the rear sleeve is only half the thickness of the balloon sidewalls, even that double thickness film is relatively thin.

BRIEF DESCRIPTION OF THE DRAWINGS

The foregoing and other objects of these inventions are illustrated more or less diagrammatically in the drawings, in which.

DETAILED DESCRIPTION OF THE INVENTION

Figure 1:
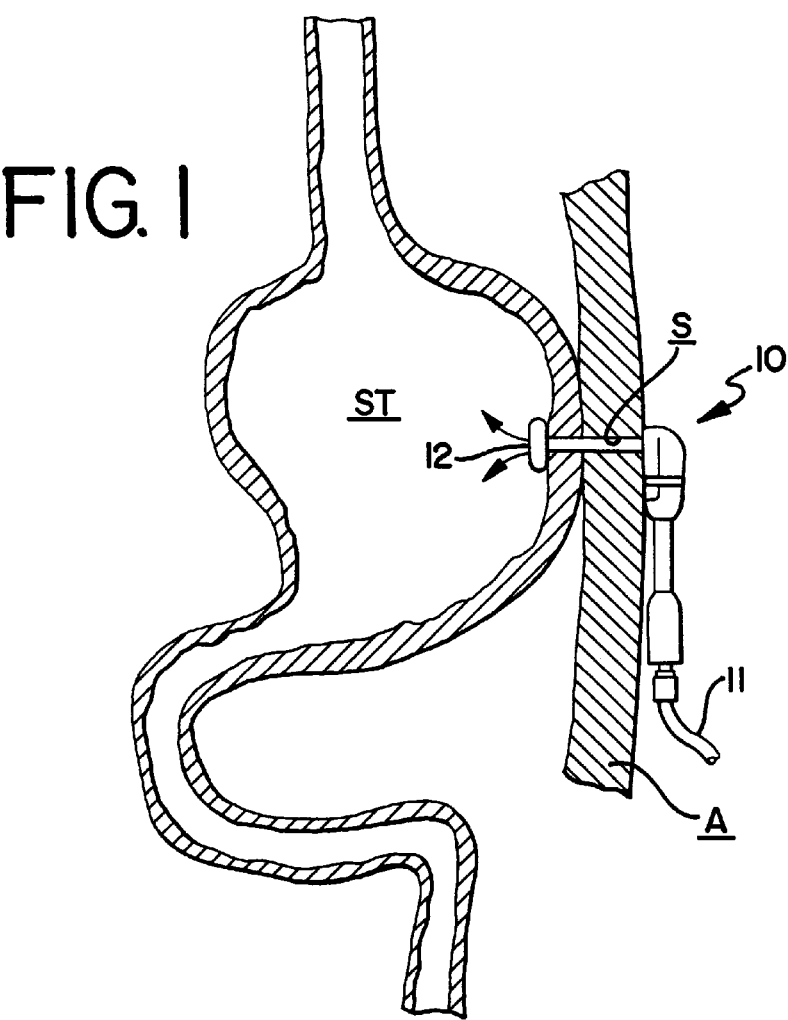
FIG. 1 is an illustration of a peg tube assembly embodying features of the invention, with the tube assembly in place accessing a patient's stomach.

Referring now to the drawings, and particularly to FIG. 1, the invention disclosed is embodied here in a peg tube assembly seen generally at 10 (with parts removed). The assembly 10 is shown in place in a patient, extending through a stoma S in the patient's abdominal wall A from a feeding formula supply tube 11 outside the abdominal wall to a discharge port 12 inside the patient's stomach ST. The stoma S may be formed in a conventional manner by one of the several well-known procedures hereinbefore referred to.

The tube assembly 10 is a peg tube assembly in the sense that has previously been described. The assembly 10 is designed to be easily connected to, and disconnected from, the conventional feeding formula supply tube 11 in a manner which is discussed in the aforementioned U.S. application Ser. No. 08/847,116, and forms no part of the present invention.

Although the invention is illustrated here in the context of a peg tube assembly 10, it may find equally advantageous application in other corporeal access tube assemblies. Jejunostomy tube assemblies, for example, or suprapubic catheter assemblies may employ the invention.

Figure 2:
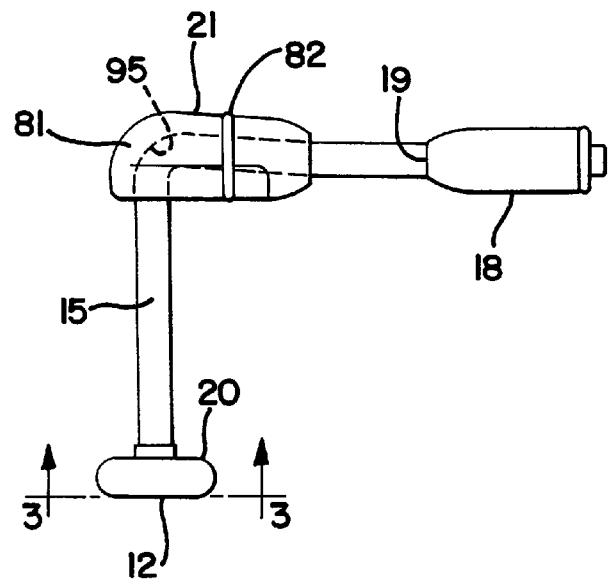
FIG. 2 is an enlarged side elevational view of the peg tube assembly illustrated in FIG. 1.

Referring now also to FIG. 2, the assembly 10 comprises a short segment 15 of tube formed from silicone rubber. The tube segment 15, which is constructed in a manner hereinafter discussed in detail, is open at one end to form the outlet port 12. A set connector 18 is connected in fluid communication with the tube segment 15 at its inlet end 19. The set connector 18 is also formed of silicone rubber.

Encircling the tube segment 15, adjacent the outlet port 12, is a tire-shaped balloon 20 which embodies features of the invention and forms an internal bolster. The balloon 20 contains gas at ambient pressure. Preferably, the gas employed is air.

Approximately intermediate the outlet port 12 and the inlet end 19 of the tube segment 15 is an external bolster 21 through which the tube segment passes. The construction and operation of the external bolster 21 is discussed in U.S. application Ser. No. 08/847,116, and forms no part of the present invention.

Figure 3:
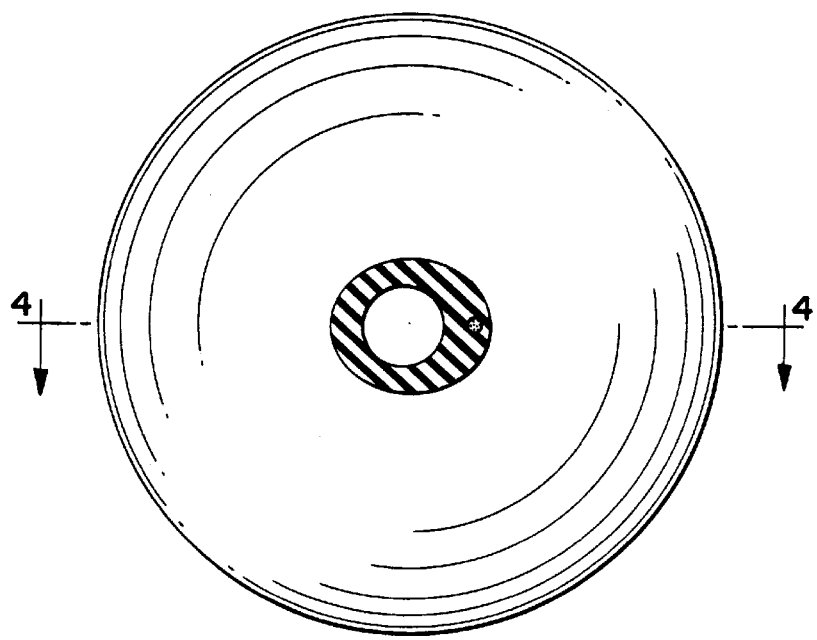
FIG. 3 is an enlarged end view taken along line 3—3 of FIG. 2.
Figure 4:
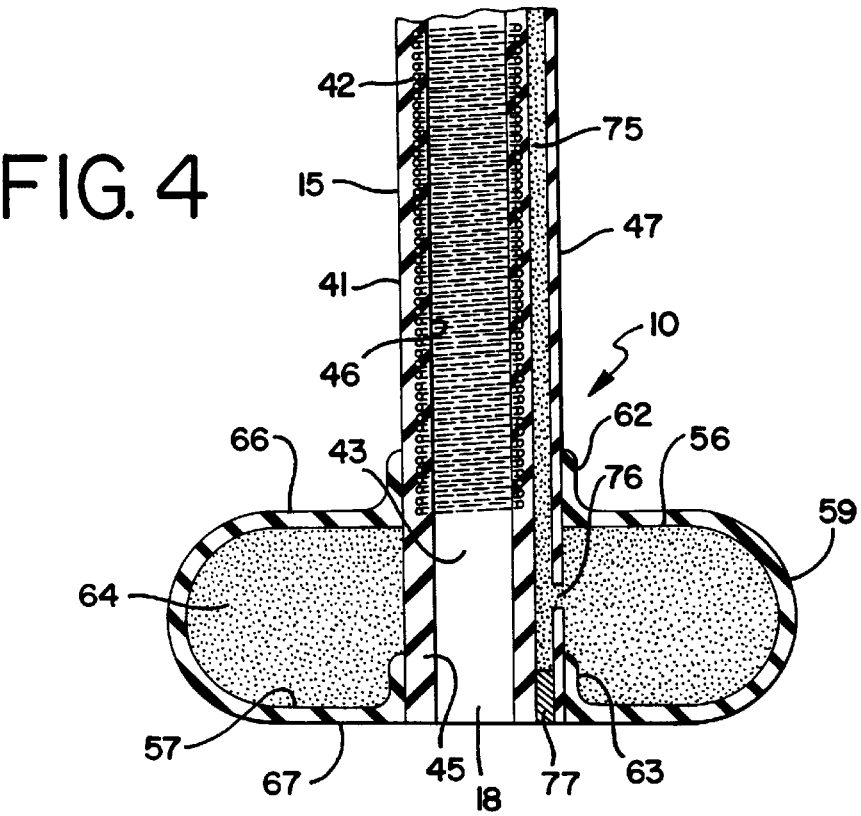
FIG. 4 is a sectional view taken along line 4—4 of FIG. 3.

Referring now to FIGS. 3 and 4, the tube segment 15 comprises a silicone body 41 containing a stainless steel wire coil spring 42. The coil spring 42 extends from the receiving end 19 of the tube segment 15 to a point 43 immediately adjacent, but not within, the balloon 20. Accordingly, the balloon 20 surrounds a tube body portion 45 which is not supported by the spring 42.

To form the tube segment 15, the coil spring 42 is inserted into an extruded silicone tube. Liquid silicone is introduced into the tube so that it flows the length of the tube, coating and covering the wire and adhering it to the inside of the tube. The liquid silicone sets to unitize the original tube, the coil spring 42 and the coating into a generally cylindrical wall having an inner surface 46 and an outer surface 47.

The tire-shaped balloon 20 is preformed in that shape from silicone rubber and includes parallel sidewalls 56 and 57. The sidewall 57 is the rear sidewall while the sidewall 56 is the front sidewall. Connecting the sidewalls 56 and 57 (in the language of tire construction) is the treadwall 59. The treadwall 59 is semi-circular in cross-section.

The annular inner peripheries of the sidewalls 56 and 57 are defined by beads 62 and 63, respectively. Each of the beads 62 and 63 comprises a cylindrical sleeve. The sleeve 63 extends forwardly of the rear sidewall 57 toward the front sidewall 56. Thus, it is inside the balloon 20. The sleeve 62 extends forwardly of the front sidewall 56. Thus, it is outside the balloon 20. The cylindrical inner surfaces of the sleeves 62 and 63 are glued to the outer surface 47 of the tube body 41 wall with a silicone adhesive.

Air is trapped in the space 64 within the preformed balloon 20 when the bead sleeves 62 and 63 are glued to the body 41 to assemble the tube 15 and balloon 20. The balloon 20 is then supported in its preformed configuration by the trapped, ambient air.

The front and rear sidewalls 56 and 57 extend parallel to each other from their corresponding bead sleeves 62 and 63 to their juncture with the semi-circular treadwall 59. A flat front surface 66 is, accordingly, defined on the outside of the front wall 56 while a flat rear surface 67 is defined on the outside of the rear wall 57.

According to the invention, the flat front surface 66 forms the balloon 20 retention surface for the assembly 10. The width of the flat surface 66, i.e., its width radially outwardly from the outside of the bead sleeve 62, equals the radius of the semi-circular outer surface on the treadwall 59. The end 43 of the coil spring 42 is aligned with the flat front surface 66 so that the spring does not extend under the balloon wall 56.

The flat rear surface 67 is flush with the tube segment 15 at its outlet port 18. Thus, the tube segment 15 does not protrude beyond the balloon 20.

In the tube assembly 10 illustrated, the body 41 of the tube segment 15 contains a deflation lumen 75 which extends the length of the tube segment between the coil spring 42 and the outer surface 47 of the tube segment body. The deflation lumen 75 communicates with the inside of the balloon 20 through a radial aperture 76 in the tube segment body 41. The lumen 75 is plugged at 77 under the balloon bead 63. It is also plugged adjacent its opposite end, i.e., at the set connector 18.

With the tube assembly 10 in place in a patient so that the retention surface 66 engages the stomach wall, and with the deflation lumen 75 plugged at both ends, the balloon 20 is substantially resistant to deformation. The tube assembly 10 cannot be inadvertently pulled out of the stoma ST without substantial effort. This result is achieved by the joint efforts of a combination of features. First, the wall thickness of the balloon is such that the balloon 20 does not stretch easily. Second, the balloon is supported by trapped air at ambient pressure. Third, the width of the retention surface equals the radius of the treadwall, giving the balloon a cross-sectional shape which, when combined with the first and second features, resists deformation.

When the lumen 75 is opened, however, as by severing the tube segment 15 near the set connector 18, air is no longer trapped in the balloon 20. The remaining tube segment 15 can be grasped adjacent the patient and the assembly 10 pulled out through the stoma ST. The balloon 20 easily folds rearwardly to make pull-out force relatively low.

To this point, the tube segment 15 and balloon 20 assembly of the invention have been described in general terms. In practice, however, the invention may be embodied in tube assemblies incorporating tubes which vary widely in French size. Balloon 20 dimensions will also vary. Accordingly, specific examples of the tube assembly 10 are hereinafter described in the context of a 20 French size tube and a 14 French size tube.

EXAMPLE 1

20 FRENCH

Figure 5:
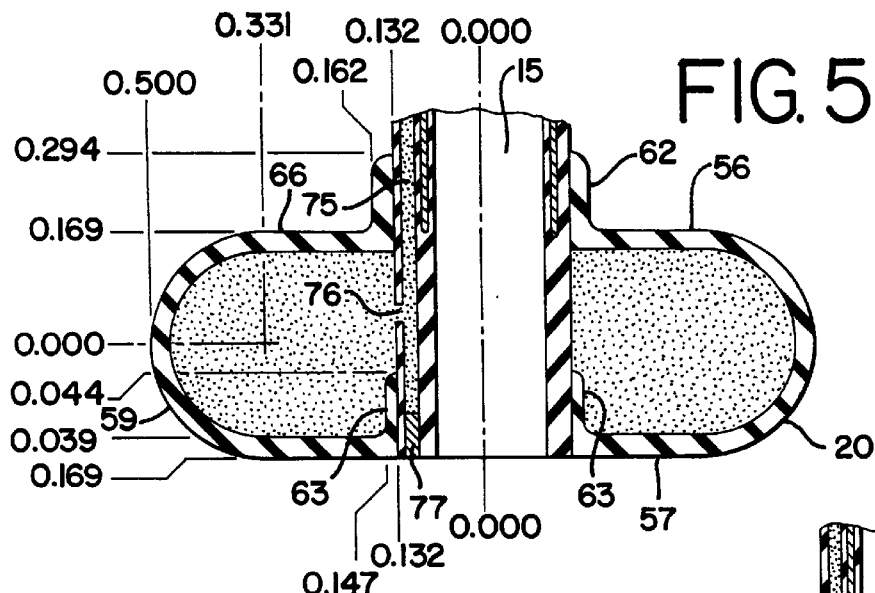
FIG. 5 is a further enlarged sectional view, similar to FIG. 4, illustrating the preferred configuration and dimensions of the balloon bolster embodying features of the invention on a 20 French tube segment and in its retention configuration.

Referring to FIG. 5, a retention balloon 20 embodying features of the present invention is shown in its retention configuration on a 20 French tube segment 15. The 20 French tube segment 15 has an outside diameter (O.D.) of 0.264 inches at its outer surface 47. The bead sleeves 62 and 63 on the balloon 20 each have corresponding inside diameters (I.D.).

In this balloon 20, the sidewalls 56 and 57 and the treadwall 59 are 0.030 inch thick silicone rubber film. The front sidewall bead sleeve 62 is also 0.030 inches thick. The rear sidewall bead sleeve 63 is only 0.015 inch thick, however. The sleeve 63 extends 0.105 inches forwardly of the front wall 57. The sleeve 62 extends 0.095 inches forwardly of the rear wall 56.

In the balloon 20 of the invention combined with a 20 French tube segment 15 to form the assembly 10, the O.D. of the balloon 20 is 1.00 inches. The distance between outer surfaces 66 and 67 of the balloon sidewalls 56 and 57 is 0.338 inches. The radius of the semi-circular tread 59 at its outer surface is 0.169 inches. This radius corresponds to the radial width of the flat retention surface 66 between the outer surface of the bead sleeve 62 and the point where the treadwall 59 curvature begins, which is also 0.169 inches.

Figure 6:
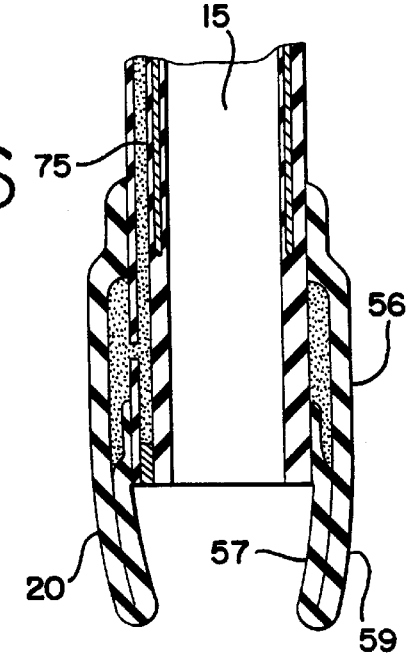
FIG. 6 is a sectional view of the balloon bolster and tube segment shown in FIG. 5, with the balloon folded rearwardly into its pull-out configuration.

Referring to FIG. 6, the retention balloon 20 of FIG. 5 is shown in its pull-out configuration. The inflation lumen 75 has been unplugged. The balloon 20 has folded rearwardly as the assembly 10 is pulled out of the stoma in a patient's abdomen, for example. The front sidewall 56 overlies the rear sidewall 57 without any bulge created by the sleeve 63.

EXAMPLE 2

14 FRENCH

Figure 7:
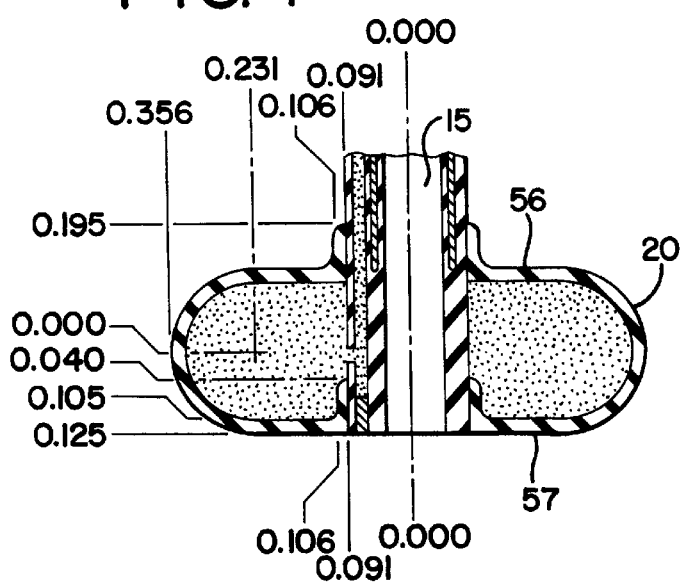
FIG. 7 is a sectional view similar to FIG. 5 but illustrating the balloon bolster of the invention on a 14 French tube segment.

Referring to FIG. 7, a retention balloon 20 embodying features of the present invention is shown in its retention configuration on a 14 French tube segment 15. The 14 French tube has an outside diameter (O.D.) of 0.180 inches at its outer surface 47. The bead sleeves 62 and 63 on the balloon 20 each have corresponding inside diameters (I.D.). The O.D. of the balloon 20 is 0.712 inches.

In this balloon 20, the sidewalls 56 and 57 and the treadwall 59 are 0.020 inch thick silicone rubber film. The front sidewall bead sleeve 62 is 0.015 inches thick. The rear sidewall bead sleeve 63 is also 0.015 inch thick, however. The sleeve 63 extends 0.070 inches forwardly of the front wall 57. The sleeve 62 extends 0.065 inches forwardly of the rear wall 56.

In the balloon 20 of the invention combined with a 20 French tube segment 15 to form the assembly 10, the distance between the surfaces 66 and 67 is 0.250 inches. The radius of the semi-circular tread 59 on its outer surface is 0.125 inches. This radius corresponds to the 0.125 inch radial width of the flat retention surface 66 between the outer surface of the bead sleeve 62 and the point where the treadwall 59 curvature begins.

Figure 8:
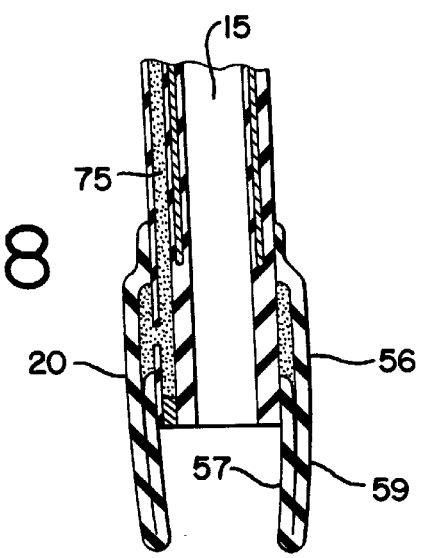
FIG. 8 is a sectional view of the balloon bolster and tube segment shown in FIG. 7, with the balloon folded rearwardly into its pull-out configuration.

Referring to FIG. 8, the retention balloon 20 on a 14 French tube segment 15 is shown in its pull-out configuration. The deflation lumen 75 has been unplugged. The balloon 20 has folded rearwardly as the assembly 10 is pulled out of a stoma. The front sidewall 56 of the balloon 20 has assumed a slim, bulge free tubular shape.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

I claim:

1. In a corporeal access tube assembly including a tube segment having an outer surface, the improvement in an internal bolster comprising:

a) a retention balloon mounted on said tube segment and being preformed so as to extend radially outwardly from said tube segment;

b) said balloon containing a gas under substantially ambient pressure which supports the balloon in said preformed configuration;

c) said balloon in said preformed configuration including a generally tire-shaped casing having front and rear sidewalls extending generally parallel to each other;

d) said balloon further including an annular, inner bead on each of said sidewalls and fastened to said outer surface of said tube segment;

e) said annular inner bead on said rear wall comprising a cylindrical sleeve extending from said rear wall toward said front wall.

2. The improvement in an internal bolster for a corporeal access tube assembly of claim 1 further characterized in that:

a) said preformed retention balloon, including said beads, is formed in one piece of silicone rubber;

b) the thickness of said sidewalls being at least 0.020 inches.

3. The improvement in an internal bolster for a corporeal access tube assembly of claim 2 further characterized in that:

a) the thickness of said rear sidewall sleeve is less than the thickness of said sidewalls.

4. The improvement in an internal bolster for a corporeal access tube assembly of claim 1 further characterized in that:

a) said balloon further includes a treadwall interconnecting said front and rear sidewalls;

b) said treadwall having an outer surface forming a semi-circle in cross-section;

c) a flat retention surface formed on said front sidewall; and d) said flat retention surface having a width which is substantially equal to the radius of said semi-circle.

5. The improvement in an internal bolster for a corporeal access tube assembly of claim 4 further characterized in that:

a) said balloon is preformed of silicone rubber.

6. The improvement in an internal bolster for a corporeal access tube assembly of claim 5 further characterized in that a) the thickness of said sidewalls and treadwall being at least 0.020 inches.

7. The improvement in an internal bolster for a corporeal access assembly of claim 6 further characterized in that a) the thickness of said sidewalls and treadwalls being about 0.030 inches.

8. In a corporeal access tube assembly including a 20 French tube segment having an outer surface, the improvement in an internal bolster comprising:

a) silicone rubber retention balloon mounted on said 20 French tube segment and being preformed so as to extend radially outwardly from said tube segment;

b) said balloon containing a gas under substantially ambient pressure which supports the balloon in said preformed configuration;

c) said balloon in said preformed configuration including a generally tire-shaped casing having front and rear sidewalls extending generally parallel to each other, and a treadwall with a semi-circular cross-section connecting them;

d) said balloon further including an annular, inner bead on each of said sidewalls and fastened to said outer surface of said tube segment;

e) said front and rear sidewalls having front and rear surfaces formed thereon, said front surface forming a flat retention surface with a radial width of about 0.169 inches.

9. The improvement in an internal bolster for a corporeal access tube assembly of claim 8 further characterized in that:

a) said treadwall has a semi-circular cross-sectional configuration and a outer surface with a radius of about 0.169 inches.

10. The improvement in an internal bolster for a corporeal access tube assembly of claim 9 further characterized in that:

a) the thickness of said sidewalls and treadwalls being about 0.030 inches.

11. The improvement in an internal bolster for a corporeal access tube assembly of claim 10 further characterized in that:

a) said annular inner bead on said rear wall comprises a cylindrical sleeve extending from said rear wall toward said front wall.

12. In a corporeal access tube assembly including a 14 French tube segment having an outer surface, the improvement in an internal bolster comprising:

a) a silicone rubber retention balloon mounted on said 20 French tube segment and being preformed so as to extend radially outwardly from said tube segment;

b) said balloon containing a gas under substantially ambient pressure which supports the balloon in said preformed configuration;

c) said balloon in said preformed configuration including a generally tire-shaped casing having front and rear sidewalls extending generally parallel to each other, and a treadwall with a semi-circular cross-section connecting them;

d) said balloon further including an annular, inner bead on each of said sidewalls and fastened to said outer surface of said tube segment;

e) said front and rear sidewalls having front and rear surfaces formed thereon, said front surface forming a retention surface with a radial width of about 0.125 inches.

13. The improvement in an internal bolster for a corporeal access tube assembly of claim 12 further characterized in that:

a) said treadwall has a shaped outer surface with a semi-circular cross-sectional configuration and a radius of about 0.169 inches.

14. The improvement in an internal bolster for a corporeal access tube assembly of claim 13 further characterized in that:

a) the thickness of said sidewalls and treadwalls being about 0.030 inches.

15. The improvement in an internal bolster for a corporeal access tube assembly of claim 12 further characterized in that:

a) said annular inner bead on said rear wall comprises a cylindrical sleeve extending from said rear wall toward said front wall.

* * * * *